United States Patent [19]
Gould et al.

[11] Patent Number: 4,572,186
[45] Date of Patent: Feb. 25, 1986

[54] VESSEL DILATION

[75] Inventors: Sheldon D. Gould, N. Miami; Gary T. Riggs, W. Palm Beach, both of Fla.

[73] Assignee: Cordis Corporation, Miami, Fla.

[21] Appl. No.: 558,910

[22] Filed: Dec. 7, 1983

[51] Int. Cl.⁴ .......................................... A61M 29/00
[52] U.S. Cl. ................... 128/341; 128/343; 604/104; 604/105
[58] Field of Search ............. 128/344, 343, 348.1, 128/341, 356, 657; 604/96, 104, 107, 105, 164

[56] References Cited
U.S. PATENT DOCUMENTS

| | | | |
|---|---|---|---|
| 1,612,697 | 12/1926 | Cecil | 128/356 |
| 2,621,651 | 12/1952 | Wallace | 128/4 |
| 2,816,552 | 12/1957 | Hoffman | 128/341 |
| 3,485,234 | 12/1969 | Stevens | 128/657 |
| 3,692,029 | 9/1972 | Adair | 604/105 |
| 3,788,318 | 1/1974 | Kim et al. | 604/164 |
| 3,789,852 | 2/1974 | Kim et al. | 604/104 |
| 3,923,065 | 12/1975 | Nozick et al. | 604/102 |
| 3,965,909 | 6/1976 | Waddell et al. | 128/348 |
| 3,968,800 | 7/1976 | Vilasi | 128/343 |
| 4,137,906 | 2/1979 | Akiyama et al. | 128/325 |
| 4,177,815 | 12/1979 | Patel | 128/344 |
| 4,195,637 | 4/1980 | Gruntzig et al. | 128/348 |
| 4,323,071 | 4/1982 | Simpson et al. | 128/343 |
| 4,465,072 | 8/1984 | Taheri | 128/348.1 |

*Primary Examiner*—Robert Peshock
*Assistant Examiner*—Cary E. Stone
*Attorney, Agent, or Firm*—Lockwood, Alex, Fitzgibbon & Cummings

[57] ABSTRACT

A vessel dilation device is provided for use within the vascular system, such device including a braided cylinder that has an adjustable axial length and that is structured such that reduction of its adjustable axial length increases its radial size in order to effect a desired extent of dilation.

24 Claims, 5 Drawing Figures

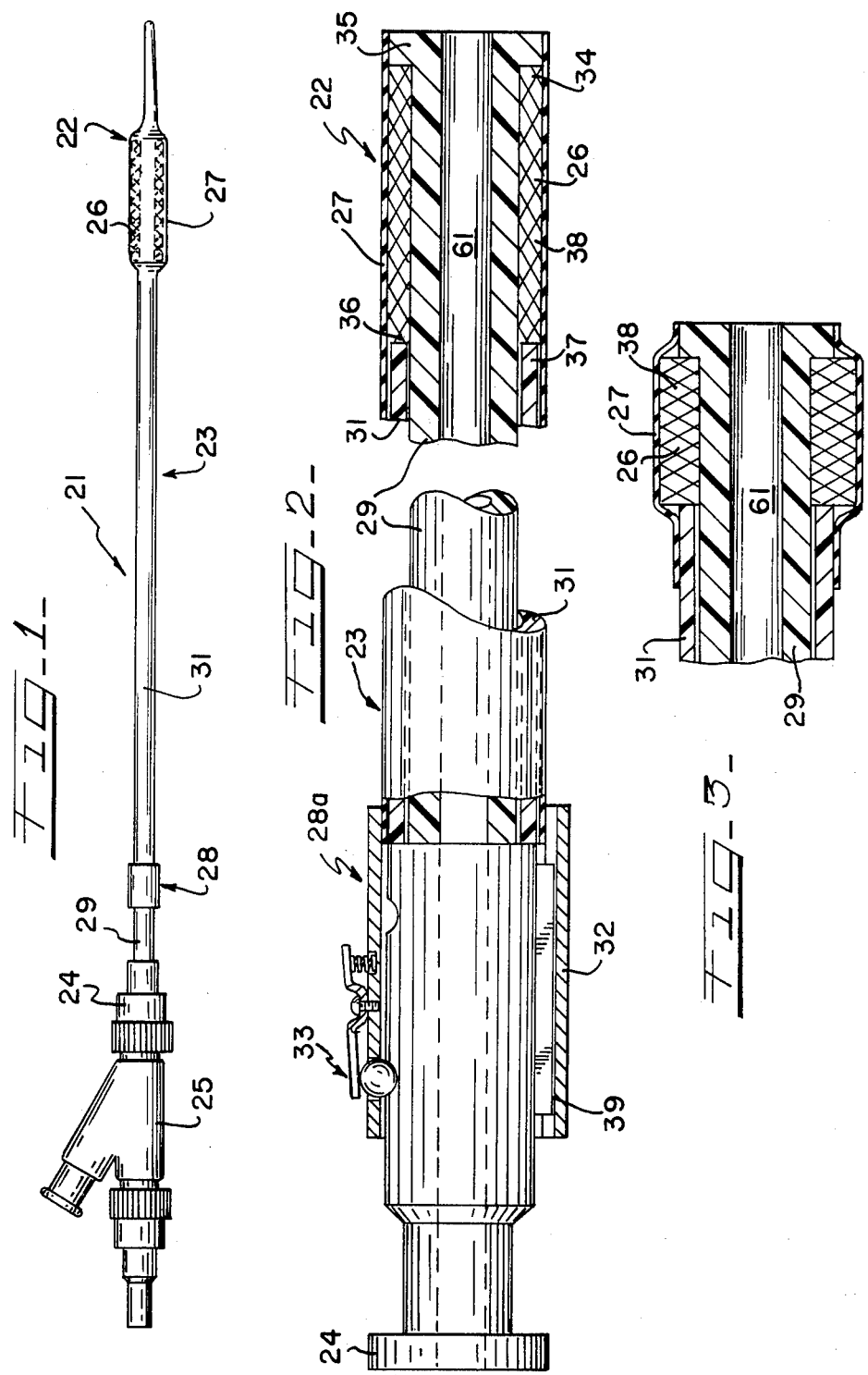

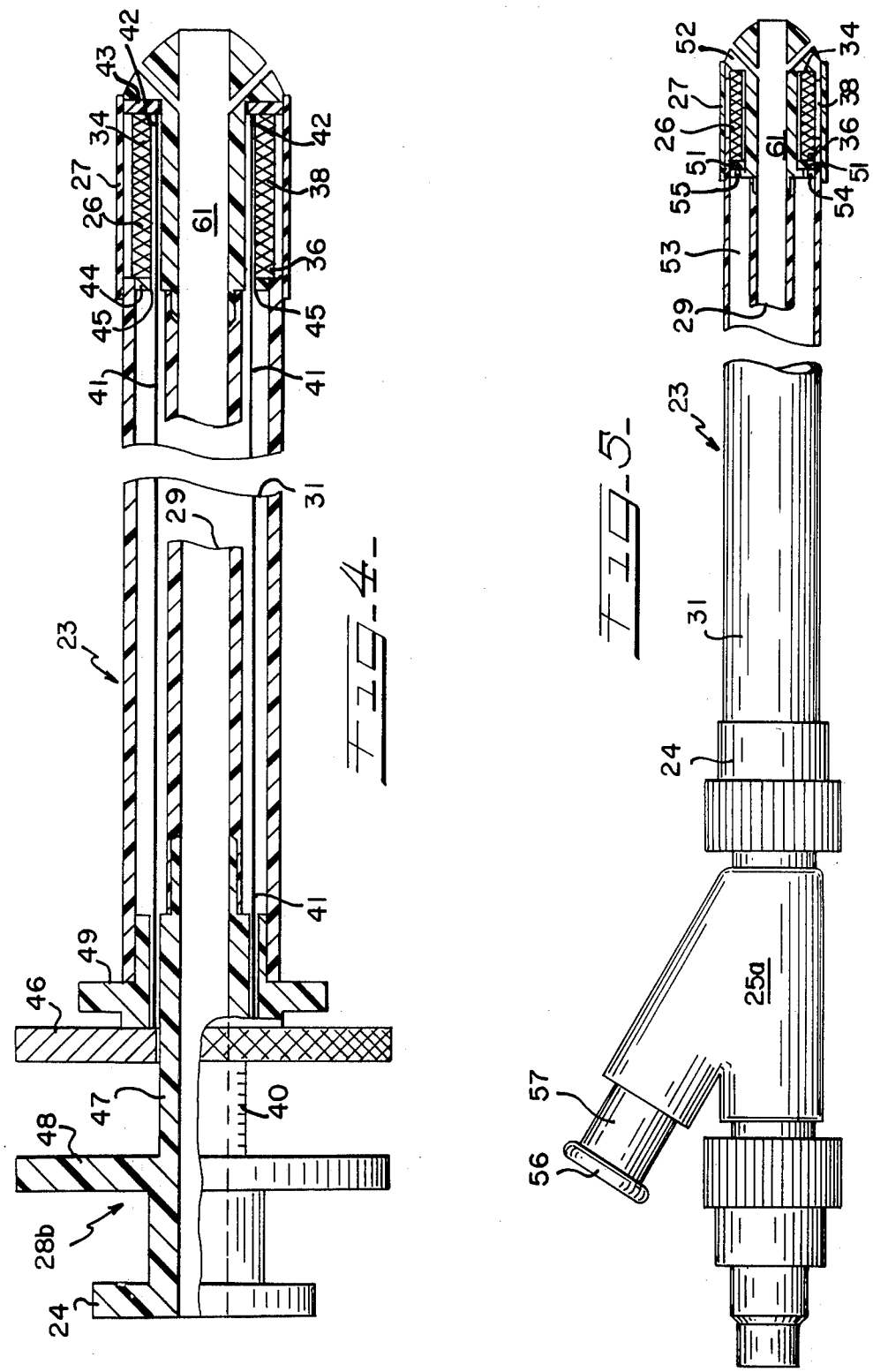

VESSEL DILATION

DESCRIPTION

This invention generally relates to dilation devices, and more particularly to dilation catheters for insertion into the vascular system and for effecting mechanical dilation therewithin. These dilation devices are characterized by including a mechanical dilation assembly that incorporates a braided cylindrical member having a variable radial size which is adjusted by varying the axial length of the braided cylindrical member.

Certain medical procedures require a catheter having an assembly at or near its distal end, which assembly is capable of increasing in radial size to beyond the outside circumference of the catheter in order to decrease an obstruction within the vascular system. Devices of this type are used in catheterization diagnostic techniques such as angiography or percutaneous transluminal coronary angioplasty. In a typical procedure, the catheter is introduced into the vascular system by way of the femoral artery until the dilation member reaches the occluded portion of a blood vessel or the like, at which time the dilation member expands in its circumferential size in order to compress the atherosclerotic material between the outside surface of the dilation member and the inside surface of the vessel in order to thereby dilate the lumen of the vessel. The atheroma is compressed, leaving a smooth, luminal surface. By the use of dilation catheters, occluded or partially obliterated sensitive hollow spaces or cavities are opened or closed as needed in accordance with the particular medical procedure being carried out.

Often, a dilation catheter is used in conjunction with a dilation assembly which includes a very small diameter elongated flexible guide and a guiding catheter that is passed over the guide. In such assemblies, the dilating catheter is inserted through the administered guiding catheter until the dilation member of the dilating catheter has passed completely through and out of the distal end of the guiding catheter and to the location where the dilation procedure is to be carried out.

Typically, the dilation element of these types of dilation catheters is of the so-called balloon type, wherein a fluid, such as a radiographic contrast liquid, is passed through the dilating catheter and into the balloon element to thereby inflate the balloon element in order to effect the dilation procedure. Such balloon elements are typically made of a generally thermoset material to the extent that the material itself does not undergo any significant expansion when subjected to hydraulic forces by the dilation fluid. Until the balloon element is thus filled with the fluid, it is folded onto itself in a collapsed condition. The balloon is in such collapsed condition as the dilation catheter is inserted into the vascular system, and, ideally, the balloon element returns to this collapsed condition before the dilation catheter is withdrawn from the vascular system.

Balloon elements have certain limitations and disadvantages. Because the balloon elements are substantially non-elastomeric, they generally do not exert adequate dilation forces until such time as they approach or actually reach their expanded size. For example, for a balloon element having a nominal dilation size of 8 mm, effective dilation would occur within a narrow range of between about 7.9 mm and 8.0 mm, inasmuch as an effective dilation pressure, for example on the order of 10 to 20 psi, would not be generated until the balloon element has been filled to that extent. Also, balloon elements are not precisely controllable by the user inasmuch as the diametric growth of the outer diameter of the balloon element as pressure increases is a function of the balloon material itself. Variations can occur depending on the evenness or unevenness with which the balloon element unfolds when it is being filled with the dilation fluid. Balloon elements also have a burst pressure which must be monitored, and the balloon elements themselves are typically not radiopaque which somewhat limits the ability of the user to precisely and consistently monitor the location of the balloon element before it is filled with the dilating fluid which may be a radiographic liquid.

Limitations and disadvantages of this type are substantially eliminated by the present invention wherein balloon elements of the type discussed hereinabove are omitted. Instead, the present invention includes a braided cylindrical member at or near the distal end of the dilation catheter, which braided cylindrical member has a radial size that is adjustable by varying the axial length of the braided cylindrical member, which variation in axial length is actuated by an assembly having a control portion at or near the proximal end of the dilation catheter.

It is accordingly a general object of the present invention to provide improved vessel dilation.

Another object of this invention is to provide an improved vessel dilation device and method which utilize a braided cylindrical member as the dilation imparting element.

Another object of the present invention is to provide an improved vessel dilation device having a braided cylinder that is typically less expensive than a molded or cast dilation balloon.

Another object of this invention is to provide an improved dilation device and method that provides enhanced radial dilating forces.

Another object of the present invention is to provide a vessel dilation device that includes a dilation element which is itself radiopaque.

Another object of the present invention is the provision of a dilation device and method that provide a dilating force that is effective over substantially the entire range of its radial expansion.

Another object of this invention is to provide an improved vessel dilation device that is substantially precisely manipulatable to an exact outer dilation size or circumference.

Another object of this invention is to provide an improved vessel dilation catheter having a dilation element that is generally cylindrical when fully collapsed and that minimizes burst pressure monitoring.

Another object of this invention is to provide an improved dilation catheter that dilates mechanically, rather than hydraulically.

These and other objects of the present invention will become apparent from the following detailed description of this invention, taken in conjunction with the accompanying drawings, wherein:

FIG. 1 is an elevational view of a typical dilation catheter according to this invention;

FIG. 2 is an elevational view, partially in cross-section, illustrating the preferred embodiment of this invention having an actuation assembly that includes coaxial shafts;

FIG. 3 is a sectional view of the distal end of the preferred embodiment, illustrating the dilation member in its expanded orientation;

FIG. 4 is a partially sectioned elevational view of an alternative embodiment; and FIG. 5 is a partially sectioned elevational view of a further embodiment according to this invention.

A typical dilation catheter in accordance with this invention is generally designated at 21 in FIG. 1 of the drawings. Included is a mechanical dilation assembly, generally designated at 22, which is mounted at the distal end of an elongated catheter shaft, generally designated at 23. The proximal end of the elongated catheter shaft 23 may include a suitable fitting such as a Luer structure 24, for attachment of the catheter 21 to a connector and/or adapter assembly 25.

The mechanical dilation assembly 22 includes a braided cylinder 26 which may be overlaid with an elastomeric sheath 27 for enhancing the smoothness of the outer surface of the braided cylinder 26. Dilation catheter 21 includes an actuation assembly having a control assembly 28 that is preferably remotely located from the mechanical dilation assembly 22. Manipulation of the control assembly 28 either increases or decreases the radial size of the braided cylinder 26 so as to vary same between its fully retracted position and its fully dilated position. Elongated catheter shaft 23 includes an inner tubular shaft 29 and an outer tubular shaft 31. In at least some embodiments, the control assembly 28 moves the outer tubular shaft 31 with respect to the inner tubular shaft 29, which movement of the outer tubular shaft 31 manipulates the mechanical dilation assembly 22.

With more particular reference to the dilation device illustrated in FIGS. 2 and 3, the outer tubular shaft 31 is movable with respect to the inner tubular shaft 29, such movement being accomplished by grasping and sliding a control collar 32 of the control assembly 28a. Preferably, the length of such relative movement is controlled by a suitable stop arrangement such as the ball-detent assembly 33 that is illustrated. Greater than two ball-detent pairs can be provided when it is desired to have additional locking settings that correspond to intermediate dilation locations of the mechanical dilation assembly 22. Other stop arrangements may be provided, such as a suitable ratchet assembly, which would permit locking of the control assembly 28a at an even greater number of dilation locations. Preferably, a keyway 39 is provided in order to prevent unintentional rotation at the location of the control assembly 28a.

Movement of the outer tubular shaft 31 translates into movement of the mechanical dilation assembly 22 for operation of the braided cylinder 26. More particularly, distal end 34 of the braided cylinder 26 is operatively secured to distal portion 35 of the inner tubular shaft 29, while proximal end 36 of the braided cylinder 26 is operatively secured to distal portion 37 of the outer tubular shaft 31. As a result, when the outer tubular shaft 31 moves in a distal direction, the spacing between the distal portion 34 of the inner tubular shaft 29 and the distal portion 37 of the outer tubular shaft 31 is decreased, thereby compressing the braided cylinder 26. As can be seen from FIG. 3, thus compressed braided cylinder 26 is increased in its radial extent in order to effect the desired degree of dilation. If a lesser degree of dilation is desired, then a spacing is selected that is between those illustrated in FIGS. 2 and 3; that is, the distance between the distal portions 35 and 37 is chosen to be less than shown in FIG. 2 and greater than shown in FIG. 3.

In order that the braided cylinder 26 will not project beyond the outside surface of the outer tubular shaft 31 before dilation is effected, a cylindrical recess 38 is provided which accommodates the uncompressed braided cylinder 26. Typically, the cylindrical recess 38 will be formed at the spacing between the location of the distal portion 37 of the outer tubular shaft 31 and the distal portion 35 of the inner tubular shaft 29.

The braided cylinder 26 includes overlapping strands that are wound over and under each other in either a generally clockwise direction or in a generally counterclockwise direction. Typically, the braiding is such that a counterclockwise strand is able to slidably and/or intersectingly move with respect to a generally clockwise strand. The braided strands should be made of a non-brittle material that can withstand, and is preferably resilient in response to, the compressive forces that are imparted to the braided cylinder 26 while it is within the cylindrical recess 38. Such materials include metals, plastics such as polycarbonates, polysulfones, polyimides, polyethylenes and the like, as well as metal strands coated with a plastic or rubber material.

Elastomeric sheath 27 that may be positioned over the braided cylinder 26 must be biocompatible and should have high elongation characteristics. Such materials include latex rubber and silicone rubber. The elongated catheter shaft 23 may be made of a suitable flexible and strong material such as polycarbonate or other materials that are utilized in catheter manufacture.

With reference to the embodiment illustrated in FIG. 4, the braided cylinder 26 is manipulated by an actuation assembly that includes one or more, for example three, actuation wires 41. The distal end 42 of each actuation wire 41 is operatively connected to the distal end 34 of the braided cylinder 26, for example by way of an annular ring 43. Proximal end 36 of the braided cylinder 26 is secured in place, such as by an annular ring 44 having passageways 45 that receive the actuation wires 41.

When the actuation wires 41 are moved in the proximal direction, the annular ring 43 moves toward the annular ring 44, which in turn moves the distal end 34 of the braided cylinder 26 toward its proximal end 36, thereby compressing the braided cylinder 26 and expanding its radial extent in order to effect the desired dilation. Movement of the actuation wires 41 in the distal direction, preferably accompanied by the elasticity of the elastomeric sheath 27 when it is expanded in the dilation mode, serves to retract the braided cylinder 26 back to its location within the cylindrical recess 38, which is the mode generally illustrated in FIG. 4.

Control assembly 28b includes suitable slides or the like for moving the actuation wires 41 in either a proximal or a distal direction. The particular control assembly 28b that is illustrated includes a slidable wire mount 46 to which the proximal ends of the actuation wires 41 are attached. Slidable wire mount 46 is slidably mounted over a hub 47. Preferably, the slidable engagement between the mount 46 and the hub 47 is one that prevents rotation of the mount 46 on the hub 47. Such may be accomplished by providing a keyway or by structuring the hub 47 and the complementary sliding surface of the mount 46 to have a non-circular cross-section such as the illustrated generally square cross-section. Preferably, hub 47 is defined by a proximal flange 48 and by a distal flange 49.

A series of graduations 40 may be provided to assist in calibrating the device for permitting precision selection of a desired dilating diameter of the braided cylinder 26. Dilation is effected by grasping the control assembly 28b with user's hand and squeezing the slidable wire mount 46 with the fingers so that the mount 46 moves toward the proximal flange 48 until the desired graduation 40 is reached or until the mount 46 engages the proximal flange 48.

With reference to the embodiment illustrated in FIG. 5, the actuation assembly thereof utilizes a liquid flow in order to decrease the longitudinal extent of the cylindrical recess 38 to thereby compress the braided cylinder 26 located therewithin and effect the desired degree of dilation. A piston 51 is provided at the proximal end 36 of the braided cylinder 26. The distal end 34 of the braided cylinder 26 is secured in place by operative attachment to the inner tubular shaft 29 through suitable operative attachment such as a flange 52.

Liquid fills an annular space 53 between the inside surface of the outer tubular shaft 31 and the outside surface of the inner tubular shaft 29, and the liquid is able to flow within the annular space 53. The liquid utilized is of the type that is suitable for use within the vascular system, including radiographic contrast liquids, saline solutinos, and the like. Compression of the liquid results in movement of the piston 51 in the distal direction, which in turn compresses the braided cylinder 26 and accomplishes the desired degree of dilation.

Preferably, a hydraulic seal 54 is provided in order to maintain the integrity of the system, such hydraulic seal 54 including one or more orifices 55 to permit liquid flow to the piston 51. Liquid enters the system and is hydraulically compressed by means of the connector and/or adapter assembly 25a, which includes a passageway (not shown) that is in hydraulic communication with the annular space 53. Hydraulic pressure is developed by a conventional structure, for example, by depressing a hand syringe 56 to a selected graduation 57.

In any of the embodiments illustrated, the inner tubular shaft 29 includes a lumen 61 that can be utilized for passage therethrough of a guiding device such as a wire guide (not shown). Lumen 61 also may be used for effecting a pressure measurement or for injection or aspiration of diagnostic and/or treatment material or the like. The mechanical dilation assembly 22 and the elongated catheter shaft 23 typically will be sized, structured and designed so that they will pass through a guiding catheter (not shown) of a dilation catheter assembly.

Braided cylinder 26 may be held in place by one or more various suitable means, such as adhesives, spot welding, soldering, or by the use of rings, collars or the like that hold the distal end 34 and the proximal end 36 of the braided cylinder 26 during movement toward and away from each other. Such rings or the like could be of various materials, such as plastic, set epoxy material, radiopaque metal, or the like.

Numerous other embodiments of this invention will be apparent to those skilled in the art without departing from the spirit and scope of this invention. Accordingly, this invention is to be defined only by the appended claims.

We claim:

1. A dilation catheter comprising:
an elonaged shaft having a proximal end and a distal end;
a mechanical dilation assembly near said distal end of the elongated shaft;
said mechanical dilation assembly including a radially and axially extending cylindrical recess, said cylindrical recess having an adjustable axial length;
a braided cylindrical member positioned generally within said cylindrical recess, said braided cylindrical member also having an adjustable axial length, said braided cylindrical member being structured such that elongation of its adjustable axial length decreases its radial size and such that reduction of its adjustable length increases its radial size; and
actuation means for elongating and reducing said adjustable axial length of the braided cylindrical member, said acuation means having control means near said proximal end of the elongated shaft.

2. The dilation catheter according to claim 1, wherein said braided cylinder is radiopaque.

3. The dilation catheter according to claim 1, wherein said mechanical dilation assembly comprises means for providing a radial dilation force over substantially the entire radial size of the braided cylindrical member.

4. The dilation catheter according to claim 1, further including an elastomeric sheath overlying said braided cylindrical member.

5. The dilation catheter according to claim 1, wherein said elongated shaft includes an inner tubular shaft and an outer tubular shaft, and wherein said control means effects movement of said tubular shafts with respect to each other.

6. The dilation catheter according to claim 1, wherein said elonaged shaft includes an inner tubular shaft and an outer tubular shaft slidably movable over said inner tubular shaft, said inner tubular shaft being operatively engaged with the distal end of said braided cylinder member, and said outer tubular shaft being operatively engaged with the proximal end of said braided cylindrical member.

7. The dilation catheter according to claim 1, wherein said elonaged shaft includes an inner tubular shaft and an outer tubular shaft slidably movable over said inner tubular shaft, said inner tubular shaft being operatively engaged with the distal end of said braided cylinder member, and said control means is for effecting the slidable movement of the outer tubular shaft.

8. The dilation catheter according to claim 1, wherein said control means includes a stop assembly for setting the actuation means at a desired position.

9. The dilation catheter according to claim 1, wherein said elongated shaft includes an inner tubular shaft and an outer tubular shaft, and wherein said cylindrical recess is located between the respective distal ends of said outer and inner tubular shafts.

10. The dilation catheter according to claim 1, wherein said actuation means includes an actuation wire having one end that is in operative engagement with said control means and having another end that is in operative engagement with said braided cylindrical member.

11. The dilation catheter according to claim 1, wherein said actuation means includes an actuation wire having one end that is in operative engagement with said control means and having another end that is in operative engagement with said braided cylindrical member, wherein said elongated shaft includes an inner and an outer tubular shaft, and wherein said actuation wire is located between said inner tubular shaft and said outer tubular shaft.

12. The dilation catheter according to claim 1, wherein said actuation means includes an actuation wire having one end that is in operative attachment with said control means and having an opposite end that is in operative attachment with the distal portion of said braided cylindrical member.

13. The dilation catheter according to claim 1, wherein said actuation means includes an actuation wire having one end that is in operative engagement with said control means and having another end that is in operative engagement with one of said braided cylindrical member, and the opposite end of said braided cylindrical member is secured in a generally stationary manner.

14. The dilation catheter according to claim 1, wherein said actuation means includes an actuation wire in operative communication with said control means and with said braided cylindrical member, and wherein said control means includes a slidable wire mount.

15. The dilation catheter according to claim 1, wherein said control means includes a series of calibration graduations.

16. The dilation catheter according to claim 1, wherein said actuation means includes a hydraulic fluid path generally between said control means and said braided cylindrical member.

17. The dilation catheter according to claim 1, wherein said actuation means includes a hydraulic fluid path generally between said control means and the proximal portion of said braided cylindrical member, and wherein the distal portion of said braided cylindrical member is secured to the catheter in a generally stationary manner.

18. The dilation catheter according to claim 1, wherein said elongated shaft includes an inner tubular member and an outer tubular member, and wherein said actuation means includes a hydraulic fluid path between said inner tubular member and said outer tubular member.

19. A method for dilating a dilation section of a vascular catheter assembly, comprising:
providing a mechanical dilation assembly near the distal end of an elongated vascular dilation catheter shaft, the mechanical dilation assembly including a braided cylindrical member;
decreasing the axial length of the braided cylindrical member to thereby correspondingly increase its radial size to a desired dilation size; and
said decreasing step including remote actuation from a location near the proximal end of the elongated shaft.

20. The method of claim 19, wherein said step of increasing the radial size of the braided cylindrical member includes imparting radial dilation forces.

21. The method of claim 19, wherein said step of increasing the radial size of the braided cylindrical member includes providing a dilating force that is effective over substantially the entire range of said increasing radial size.

22. The method of claim 19, wherein said decreasing step includes axially moving one tube of the catheter shaft with respect to another tube thereof.

23. The method of claim 19, wherein said decreasing step includes applying a pulling force to a wire.

24. The method of claim 19, wherein said decreasing step includes hydraulic actuation.

* * * * *